United States Patent [19]

Glaug et al.

[11] Patent Number: 4,701,178
[45] Date of Patent: Oct. 20, 1987

[54] SANITARY NAPKINS WITH FLAPS

[75] Inventors: Frank S. Glaug, Spotswood; Thomas J. Luceri, Bridgewater; Deborah J. Parr, Plainsboro, all of N.J.

[73] Assignee: Personal Products, Inc., Milltown, N.J.

[21] Appl. No.: 936,683

[22] Filed: Dec. 1, 1986

[51] Int. Cl.$^4$ .............................................. A61F 13/16
[52] U.S. Cl. ..................................... 604/387; 604/389
[58] Field of Search ..................... 604/386, 387, 385.1, 604/389, 390, 391

[56] References Cited

U.S. PATENT DOCUMENTS

| 4,596,570 | 6/1986 | Jackson et al. | 604/387 |
| 4,605,405 | 8/1986 | Lassen | 604/385.1 X |
| 4,608,047 | 8/1986 | Mattingly | 604/387 |
| 4,615,696 | 10/1986 | Jackson et al. | 604/389 |

Primary Examiner—John D. Yasko
Attorney, Agent, or Firm—Wayne R. Eberhardt

[57] ABSTRACT

An absorbent product has a central absorbent element. Flaps extend from each of the longitudinal edges of the product. Pressure sensitive adhesive is centrally located on the garment facing side of the product and on the garment facing side of the flaps. A single release strip has a first side covering the centrally located adhesive. The flaps are folded over the release strip with the flap adhesive contacting the second side of the release strip.

18 Claims, 13 Drawing Figures

SANITARY NAPKINS WITH FLAPS

This invention relates to absorbent products for absorbing body fluids, and in particular, to such products intended to be worn against the perineal portion of the body and held in place by attachment to the crotch portion of the undergarment worn by the user. Such products find wide application as sanitary napkins, panty shields, panty liners, and adult incontinence pads.

Recent advances in absorbent products which attach to the undergarment of a user have been directed toward solving problems involving secure placement of the product and soiling of the user's body and clothing. U.S. Pat. No. 4,608,047 for example shows a sanitary napkin comprising a central absorbent element having flaps extending from each of its longitudinal edges. In use the absorbent element of the napkin is placed in the inner crotch portion of the user's undergarment. Pressure-sensitive adhesive lines on the garment-facing side of the napkin are employed to retain the napkin in its desired position in the undergarment. The edge flaps are then folded about the crotch portion so as to overlie the outer crotch portion of the undergarment. One or both of the flaps have pressure-sensitive adhesive located thereon so that when the flaps overlie each other the napkin securely surrounds the crotch portion of the undergarment.

This form of construction of the absorbent product affords several advantages. By using fluid impermeable material in the flaps, soiling of the undergarment is deterred, since the crotch portion of the undergarment is surrounded by a fluid impermeable barrier. The flaps may additionally include an absorbent material on their body-facing sides to retard fluid seepage around the edges of the crotch portion of the undergarment. Furthermore, when the flaps are made of flexible materials, they can be folded as appropriate to conform to the dimensions of the user's undergarment. The form-fitting characteristic of the absorbent product retards wrinkling and uncertain securement of the product.

A variation of the above-described absorbent product is to size the flaps to extend a shorter distance from the central absorbent element such that the flaps will generally not overlie each other when folded about the outer crotch portion of the undergarment. Sanitary napkins having flaps with this characteristic are shown, for example, in U.S. Pat. Nos. 4,285,343 and 4,589,876. These napkins are worn by adhesively securing the central absorbent element of the napkin to the inner crotch portion of the undergarment, then folding the flaps around the edges of the crotch portion of the undergarment and adhesively securing the flaps to the outer crotch portion of the undergarment. The flaps do not overlap, but are individually adhesively secured in place. Accordingly, these sanitary napkins are provided with pressure-sensitive adhesive on the garment-facing side of the central absorbent element and on the garment-facing side of each of the flaps.

When absorbent products are produced with pressure-sensitive adhesive for attaching the product to a user's undergarment, it is conventional to overlie the adhesive with protective release strips. The release strips are removed just prior to use of the product, and act to protect the adhesive from dirt and unintended adhesion during manufacture, packaging and storage. The conventional wisdom in the design of flapped absorbent products with adhesive on the central absorbent element and on each of the flaps is to place a separate release strip over each area of adhesive, as shown in U.S. Pat. Nos. 4,285,343 and 4,589,876. This, however, presents the user with a cumbersome process when preparing the product for use. The user must prepare the product by removing all three release strips, as compared with the single release strip of prior art absorbent products which lack flaps. Care must be taken when removing the strips so that the flaps do not inadvertently adhere to each other or another part of the product as the strips are being removed. In particular, the user must carefully handle the product when removing the release strip on one flap, lest the other flap inadvertently fold over the exposed adhesive on the central absorbent element and adhere there. Such an accident could render the product useless, especially if the exposed adhesive on the other flap contacts the adhesive on the central absorbent element. Even when the problem of undesired adhesion is avoided, the user is then presented with the task of disposing of three release strips.

In addition to the user problems, the use of three release strips is wasteful of release strips material. One expedient to cure the problem of three strips would be to cover the entire garment facing side of the absorbent product with one large release strip overlying all three adhesive areas. However, such an expedient would be wasteful of even more release strip material, and could cause even more substantial inadvertent adhesion problems when the release strip is pulled upward from the garment-facing surface of the product. This pulling action would pull the flaps upward also, and into a position where they could easily fold downward onto the adhesive of the central absorbent element.

In accordance with the principles of the present invention, an absorbent product with edge flaps is provided which has adhesive located on the garment facing side of a central absorbent element and on the garment facing side of one or both of the edge flaps. A protective release strip is located with one side overlying the adhesive on the central absorbent element. The edge flaps are folded over the release strip with the adhesive on the edge flaps located on the other side of the release strip. This absorbent product conserves the use of release strip material, and also affords an ease of release strip removal which reduces problems of unintended adhesion.

Figure 1:
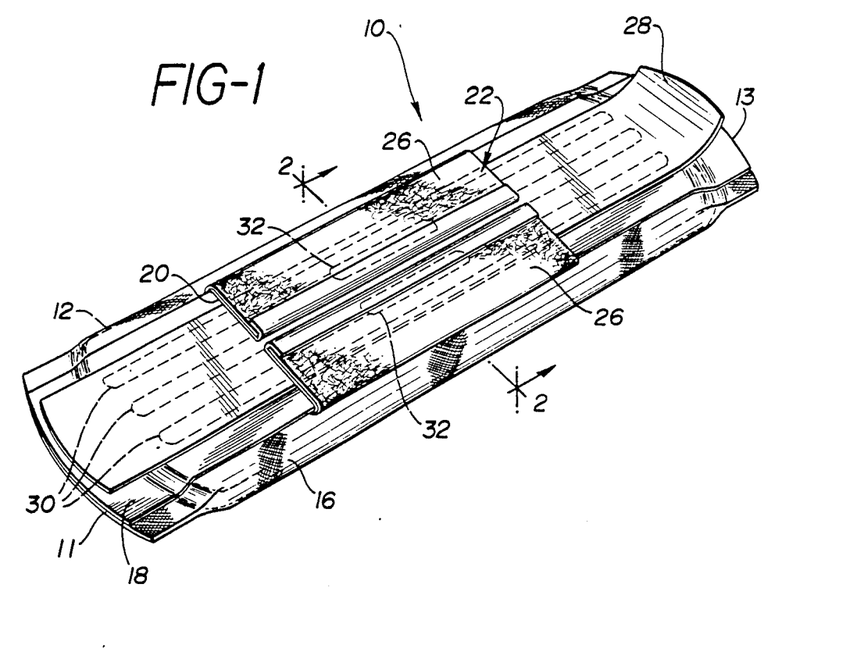
FIG. 1 illustrates a sanitary napkin constructed in accordance with the principles of the present invention.
Figure 2:
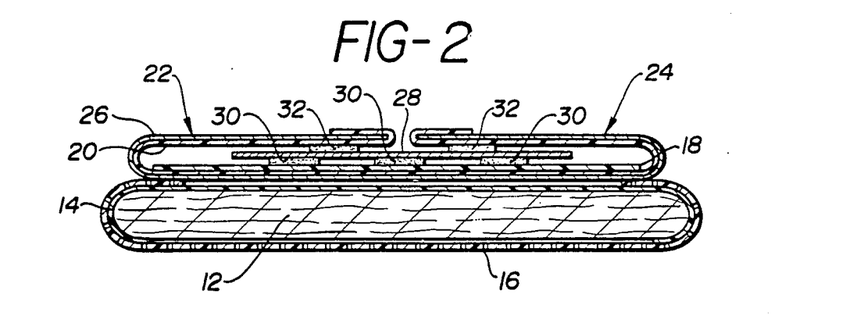
FIG. 2 is a cross-sectional view of the sanitary napkin of FIG. 1 taken along lines 2—2.

Referring to FIGS. 1 and 2, a sanitary napkin 10 constructed in accordance with the principles of the present invention is shown. The napkin 10 is provided with a centrally located absorbent element 12 having generally longitudinally extending edges and transversely extending ends 11 and 13. The absorbent element 12 may be comprised of any of the well known absorbent materials used in products for absorbing body fluids such as, for example, loosely associated absorbent hydrophilic material such as cellulose fibers. e.g. wood pulp, regenerated cellulose or cotton fibers. Such fibers may be chemically or physically modified and the absorbent element may include such fibers in combination with other materials, both natural and synthetic, such as hydrophilic foams, hydrophilic polymers or the like. Wood pulp is frequently the material of choice primarily because it is inexpensive and readily available.

The absorbent element may also comprise layers of materials which in the aggregate are body fluid absorbent. For example the outermost layer (closest to the body) may be a resilient, relatively non-absorbing, fluid previous material. Such a material is provided for comfort and conformability and directs fluid to an underlying layer, e.g. wood pulp, which retains such fluid. A useful material for this outer layer is hollow polyester fibers having a denier of about 8.5 and a length of about 1.5 inches.

Overlying the absorbent element 12 is a fluid permeable cover material 16. This cover may comprise any of the well known cover materials used in sanitary napkins including, for example, non-woven fabrics of cellulose, regenerated cellulose, polyester or other synthetic polymers. Additionally, polymeric fibers or films having apertures therethrough to render the materials previous to fluids may also be employed. A cover material of choice is a fabric comprising heat bondable polyester/polyethylene conjugate fibers.

The absorbent element 12 is wrapped in and adhered to a C-shaped wrap 14 of fluid impervious material. The fluid impervious material comprises a polyethylene "boat" 14, which is adhered to the absorbent element by an emulsion adhesive. The purpose of the polyethylene boat 14 is fluid containment, whereby fluid will not be transferred from the garment facing side and edges of the absorbent element to an outer location where it could stain the undergarments of the user.

The cover material 16 surrounds the absorbent element and polyethylene boat in a C-shaped wrap which extends beyond the longitudinal ends of the absorbent element. The cover is sealed at the ends 11, 13 and adhered at the ends and longitudinally to a body fluid impervious barrier 18. The barrier 18 is provided to preclude body fluid from passing onto the undergarment of the wearer. Barrier 18, like the wrap 14, may be any polymeric film such as polyethylene, polypropylene, or cellophane or may be a normally fluid-pervious material that has been treated to be impervious such as a fluid repellent paper. When the cover 16 and the barrier 18 are made of heat bondable materials the cover 16 may be advantageously thermally sealed at its ends and to the barrier 18.

Located in the center of the napkin 10 is a sheet of fluid impervious barrier material 20. The barrier material 20 may comprise the same or similar barrier material as the barrier 18. A layer of absorbent material 26 is laminated to the body facing surface of the barrier material 20. The barrier material 20 with its layer of absorbent material 26 is located between the barrier 18 and the cover and polyethylene boat and is adhered in place, with flaps 22 and 24 extending out from the longitudinal edges of the barrier 18. As will become apparent from the further description, flaps 22 and 24 extended a sufficient degree to enable the flaps to overlie the outer crotch portion of the wearer's undergarment. Flaps 22 and 24 are provided for two primary purposes, namely: to more fully protect the user's undergarment from liquid escaping from the absorbent element 12 at its longitudinal edges and to act as an attachment system to hold the absorbent element 12 firmly in place and have element 12 move together with the crotch of the garment as the latter moves responsive to the wearer's movements.

Absorbent material 26 may comprise a thin, absorbent layer of material such as tissue, fabric or the like made of cellulosic fibers. This material is provided so that escaped fluid from the element 12 may be absorbed and prevented from flowing across the flaps and onto the body or garment of the weater. Since the absorbent material layer 26 covers the body-facing side of the flaps, it also provides a degree of comfort in the crotch area of the user's undergarment. Because such material is provided as a safety measure and is only required to retain escaped fluid, it need not be very absorbent at all and, in fact, may be comprised of any capillary or cellular system including hydrophobic material. Thus, a useful material may be a 0.5 oz./yd.$^2$ fabric comprised of hollow polyester fibers and heat bondable polyester/polyethylene conjugate fibers. Such conjugate fibers are fibers which comprise a polyester core surrounded by a sheath of polyethylene. Although it is not composed of hydrophilic fibers, such a material may be formed of a sufficiently fine capillary structure so as to retain small quantities of escaped liquid and hence be sufficiently "absorbent" for its intended purpose as a safety measure.

When the absorbent layer 26 and the barrier material ZO are both formed of thermoplastic material as described above, the napkin 10 may be advantageously assembled by heat sealing. The absorbent layer surface of the flaps is thermally sealed to the opposing longitudinal edges of the cover 16, and the barrier material 20 of the flaps is thermally sealed to the opposing edges of the barrier 18. In a preferred embodiment the barrier 18 and the barrier In a preferred embodiment the barrier 18 and the barrier material 20 comprise sheets of 1.5 mil embossed polyethylene.

Disposed on the garment facing surface of the barrier 18 are longitudinally extending pressure-sensitive adhesive means 30, provided for attaching the napkin to the inner crotch portion of an undergarment. While such adhesive means are illustrated in the form of longitudinally extending lines, it will be understood that various patterns such as spots, squares, or transverse lines are suitable. The adhesive employed may be any of the large number of pressure-sensitive adhesives that are commercially available, including water based adhesives such as acrylate adhesives, e.g., vinyl acetate/2-ethylhexyl acrylate copolymer which may be combined with tackifiers. Alternatively, the adhesive may also comprise a pressure-sensitive rapid-setting hot melt adhesive such as Fuller 6680 produced by the H.B. Fuller Co. The adhesive means may also comprise a double faced tape.

Disposed on the garment facing sides of the flaps 22, 24 (i.e., the sides opposite those which are covered by layer 26) are pressure-sensitive adhesive means 32. These adhesive means are provided for attaching the flaps to the outer crotch portion of the undergarment. They may be formed in a similar variety of shapes and of a like variety of materials as the adhesive means 30.

In accordance with the principles of the present invention, overlying the adhesive means 30 is a protective release strip 28 which is provided to protect the adhesive means from dirt and unintended adhesion prior to use. The release strip 28 may be constructed of any suitable sheet-like material which adheres with sufficient tenacity to the adhesive means to remain in place prior to use but which can be readily removed when the napkin is to be used. A particularly useful material is a semibleached kraft paper, the adhesive contacting side of which has been silicone treated to provide easy release from the adhesive means 30. Other useful materials include 58 lbs./ream or 35 lbs./ream calendered paper.

The release strip 28 also provides protection for adhesive means 32 on the flaps 22 and 24. As shown in FIG. 1, the flaps are folded over and adhered to the opposite side of the release strip from the side contacting adhesive means 30. Since both sides of the release strip 2B are in contact with adhesive means, both sides of the release strip are silicone treated for easy release from adhesive means 30 and 32. The use of a single release strip protecting the three adhesive areas of the napkin conserves the amount of release strip material needed for the napkin, requires the user to dispose of only a single release strip, forms a compact napkin with folded over flaps that is easy to package, and affords an ease in preparation for use that deters inadvertent adhesion, as will be more fully understood by referring to FIGS. 3a-3c.

Figure 3A:
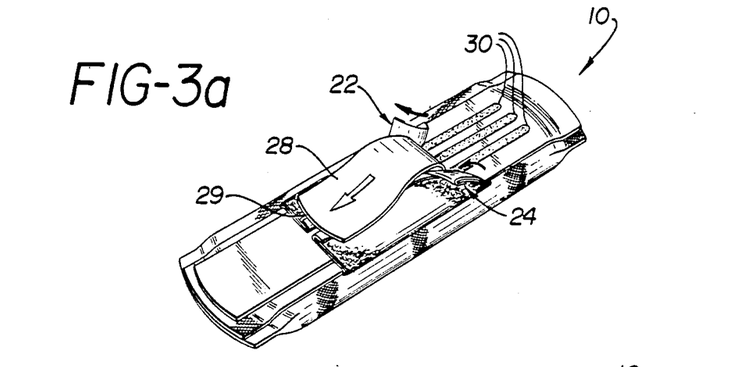
FIGS. 3a–3c illustrate a step-wise process for removing the release strip from the sanitary napkin of FIG. 1.

Just prior to use of the napkin 10 of FIG. 1, the user grasps one end 29 of the release strip 28 and begins peeling the release strip away from the adhesive means 30 on the barrier 18, as indicated by the directional arrow. As the removal of the release strip reaches the central area of the napkin where the flaps overlie the release strip, the upward motion of the peeling release strip lifts up the ends of the flaps 22 and 24 as shown in FIG. 3a, and begins to fold them back toward their opened position.

Figure 3B:
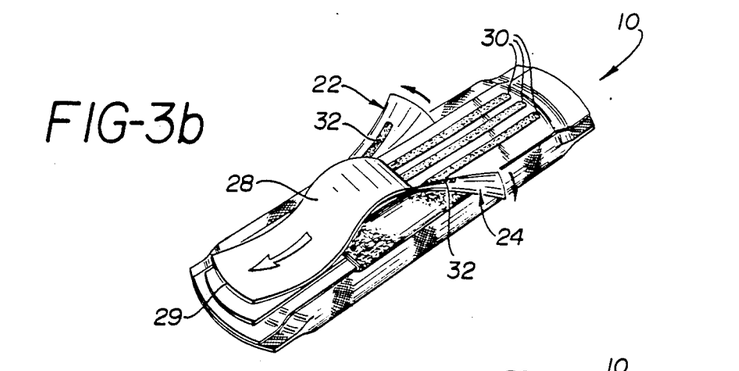

As the peeling process continues as shown in FIG. 3b, the upward motion of the release strip 28 continues to lift and spread the previously folded flaps 22 and 24. As can be seen in FIG. 3b, the continuation of the peeling process to the illustrated stage has begun to reveal the adhesive means 32 on flaps 22 and 24.

Figure 3C:
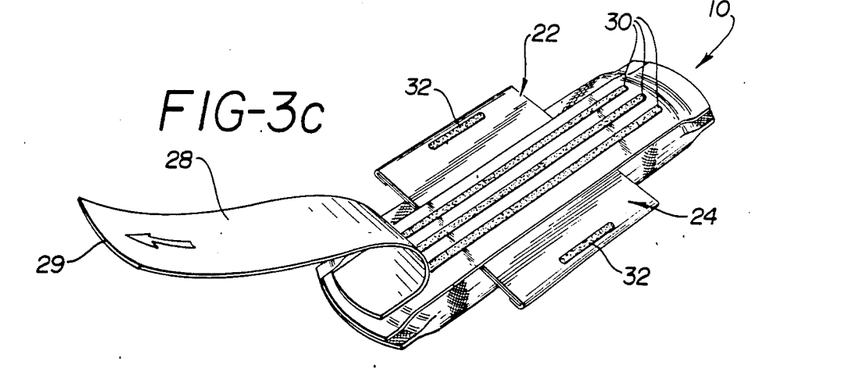

In FIG. 3c, the continuation of the peeling process has passed beyond the central flap area of the napkin, leaving the flaps 22 and 24 splayed in their open position. Thereafter the release strip 28 is completely removed from the adhesive means 30 and the napkin is ready for application to the user's undergarment. This is accomplished by adhering adhesive means 30 to the inner crotch portion of the user's undergarment, folding the flaps 22 and 24 over the edges of the crotch portion, and the undergarment, as more fully described in U.S. Pat. No. 4,608,047.

Figure 4A:
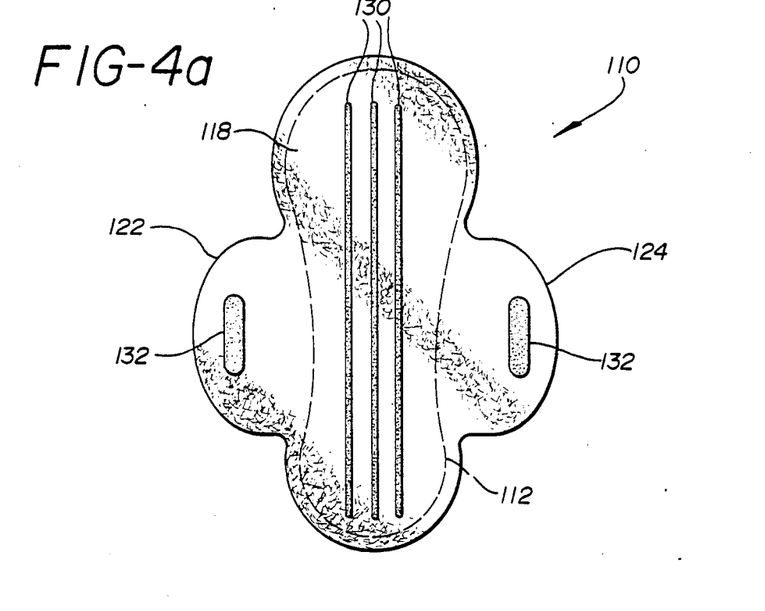
FIGS. 4a and 4b illustrate a second embodiment of the present invention.
Figure 4B:
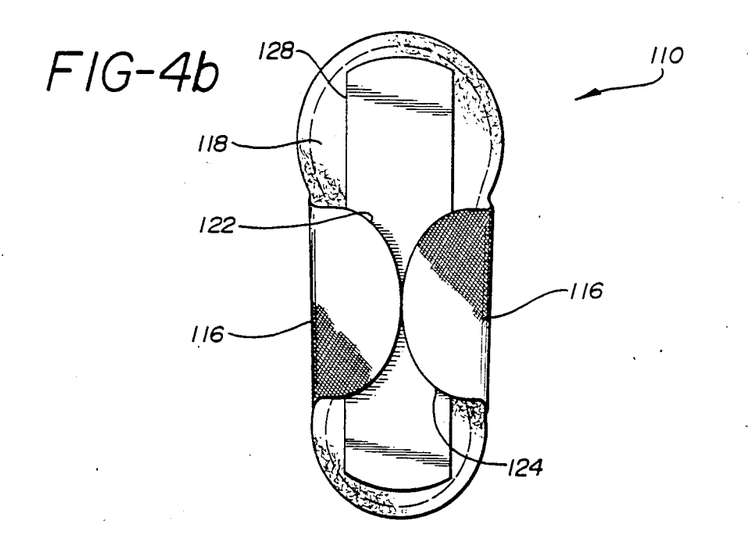

Referring to FIGS. 4a and 4b, a sanitary napkin 110 constructed in accordance with the principles of the present invention and utilizing the teachings of U.S. Pat. No. 4,608,047, hereby incorporated by reference, is shown in plan views. FIG. 4a shows the garment facing side of the napkin 110, which is completely covered by a body fluid impervious barrier 118. This side of the central absorbent element area of the napkin, outlined by dashed line 112, and the flaps 122 and 124 are covered with an appropriately shaped extension of the barrier 118, which may comprise any of the materials suitable for barrier 18 of FIG. 1. Adhesive means 130 are located on the central portion of the barrier, and adhesive means 132 are located on each of the flaps 122 and 124.

Underlying the absorbent element of napkin 110, between the absorbent element and the barrier 118, is a thin layer of absorbent material comprised of materials suitable for use as layer 26 of FIG. 1. This layer of absorbent material extends beyond the area of the absorbent element to the degree that it is coextensive with the flaps 122 and 124. The layer of absorbent material is thus of the same general shape as the barrier 118.

Overlying both the absorbent element and the thin layer of absorbent material on the body facing side of the napkin 110 is a fluid permeable cover material 116, visible on the flaps 122 and 124 in FIG. 4b. The cover material 116 may comprise the same materials suitable for cover 16 of FIG. 1. Like the thin layer of absorbent material, the cover material 116 is coextensive with flaps 122 and 124. The thin absorbent layer and the overlying cover material 116 thus comprise material layers on the body facing side of the flaps which will entrap any body fluid which escapes from the sides of the absorbent element. The use of a thermoplastic material for cover material 116 in conjunction with a thermoplastic barrier for flaps 122 and 124 permit the entire napkin 110 to be stabilized and heat sealed about the periphery of the napkin.

FIG. 4b shows napkin 110 with a release strip 128 located with one side in contact with the adhesive means 130. The flaps 122 and 124 are folded onto the other side of the release strip 128 so that adhesive means 132 contact the release strip. When the release strip 128 is removed as in the manner shown in FIGS. 3a-3c, the flaps 122 and 124 will be splayed in the same fashion as illustrated in those FIGURES.

Figure 5A:
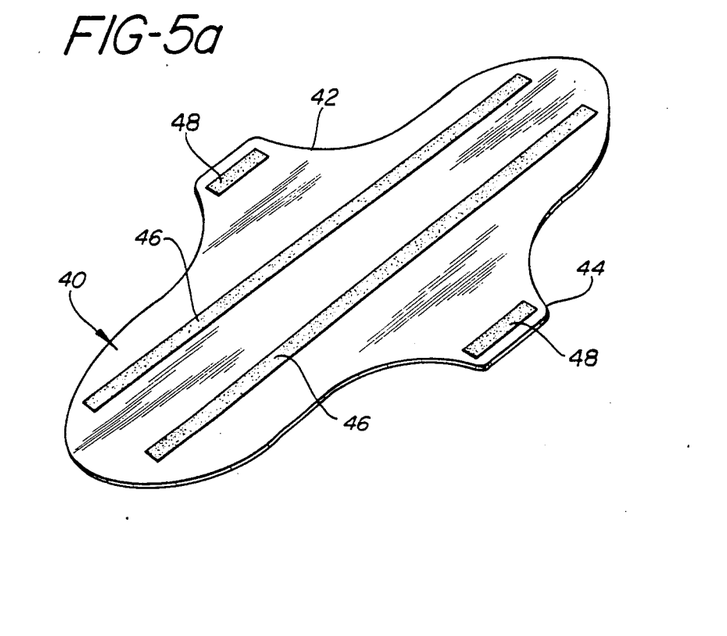
FIGS. 5a and 5b illustrate a panty shield constructed in accordance with the principles of the present invention.
Figure 5B:
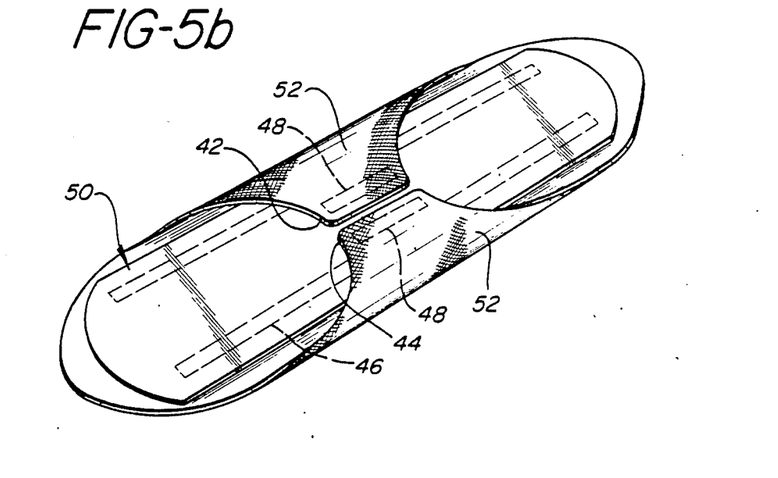

FIGS. 5a and 5b illustrate a panty liner 40 constructed in accordance with the principles of the present invention. The liner is formed of a laminate of a polyethylene sheet and an open weave blend of bicomponent fusible fibers and rayon. The polyethylene side is the side facing upward in FIG. 5a, and the side comprising the open weave blend is indicated at 52 in FIG. 5b. The polyethylene sheet has a thickness in the range of 1 to 5 mils, and preferably in the range of 1 to 1.5 mils. The open weave blend is a blend of 80% polyester/polyethylene (e.g. Enka fibers) and 20% rayon. The blend is only a few fiber layers thick, having a weight, for instance, of about 1-2 oz./yd$^2$ and provides the body-facing side of the liner with a soft esthetic feel and look. If desired, the body facing side may comprise hydrophilic materials for greater absorptive properties, allowing that side of the liner to entrap and retain small quantities of body fluid.

Two lines 46 of an adhesive means are located on the garment facing side of the panty liner as shown in FIG. 5a. Extending from the central area of the liner are flaps 42 and 44, each of which has a line 48 of adhesive means affixed near the distal end of the flap. In accordance with the principles of the present invention a release strip 50 is located on the central area of the panty liner to protectively and releasably cover the adhesive lines 46. Flaps 42 and 44 are folded over the release strip 50 and adhesive lines 48 are releasably affixed to the upward facing side of the release strip 50, as shown in FIG. 5b. The use of the single release strip thereby forms the panty liner into a compact package while being stored prior to use.

Figure 6A:
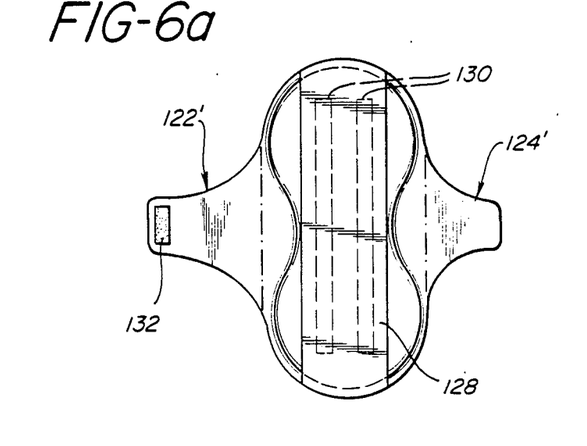
FIGS. 6a–6d illustrate a further embodiment of the present invention.

Referring to FIGS. 6a-6d, a sanitary napkin similar to that of FIGS. 4a and 4b is shown, which employs adhesive means 132 on only one flap. Located proximate the central absorbent element area of the napkin and on the barrier 118 are two lines 130 of a dual track positioning hot melt adhesive. Overlying the adhesive 130 is the release strip 128. Extending from either side of the central absorbent element area of the napkin as shown in FIG. 6a are two flaps or side panels 122' and 124'. The side panel 122' extends farther from the central absorbent element area of the napkin than the smaller side panel 124'. The side panel 122' has one line 132 of a single track positioning hot melt adhesive located near its end on the garment facing (barrier) side of the panel.

Figures 6B, 6C, 6D:
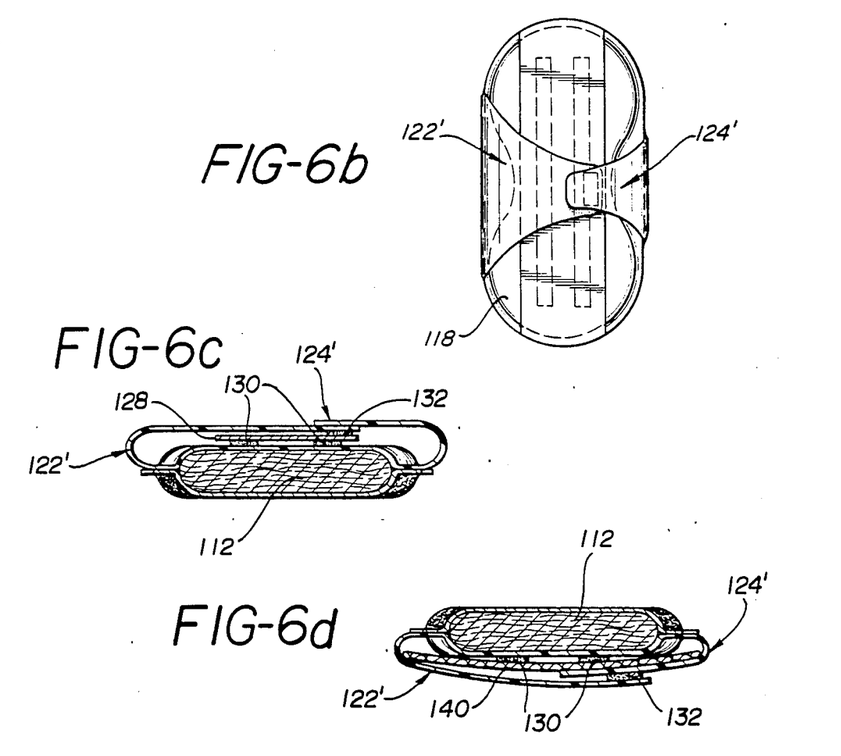

The napkin is shown in its folded condition in accordance with the principles of the present invention in FIGS. 6b and 6c. The large side panel 122' is first folded over the release strip 128 with its adhesive track 132 adhered to the release strip. The small side panel 124' is then folded loose over the large panel. FIG. 6c is a cross-sectional view taken through the center of the napkin in its folded condition which shows the ordering of the various adhesive tracks and side panels above the central absorbent pad 112.

FIG. 6d shows the napkin of FIGS. 6a–6c when positioned for use in the crotch region of the undergarment 140 of a user. After the release strip 128 has been removed, the absorbent pad is positioned in place by adhering the dual track positioning adhesive 130 to the inner crotch portion of the undergarment 140. The small side panel 124' is then folded around one edge of the undergarment to the outer crotch portion of the undergarment. Finally, the large side panel 122' is folded around the other edge of the undergarment and secured to the outside of the small side panel by the single track positioning adhesive 132. The crotch region of the undergarment is thereby completely protected by its wrapping of the two side panels of the napkin. The two side panels will not wrinkle or bind with movement of the undergarment, since they are not adhered to the undergarment. Instead, the two side panels will move slightly along the outer crotch portion of the undergarment in correspondence with the motion and position of the user and the undergarment. The absorbent pad 112 will not move from its intended position because it is secured in place by adhesive tracks 130.

What is claimed is:

1. An absorbent product having oppositely disposed ends and longitudinal edges, comprising:
    a central absorbent element having a body facing side and a garment facing side;
    a sheet of fluid impervious barrier material disposed on the garment facing side of said absorbent element and having an element facing side opposing said absorbent element and a garment facing side;
    a pair of flaps extending respectively from the longitudinal edges of said product and having body facing sides and garment facing sides;
    adhesive means located on the garment facing side of said barrier material and on the garment facing side of at least one of said flaps: and
    a release strip having a first side overlying said barrier material adhesive means and a second side, wherein those of said flaps having adhesive means located thereon are folded over said strip with said flap adhesive means contacting the second side of said release strip.

2. The absorbent product of claim 1, further comprising a cover disposed on the body facing side of said absorbent element.

3. The absorbent product of claim 2, further comprising a layer of absorbent material overlying the body facing sides of said flaps.

4. The absorbent product of claim 1, wherein adhesive means is located on the garment facing side of both of said flaps.

5. The absorbent product of claim 4, wherein said release strip is formed of a material which allows said adhesive means to be readily removed from said release strip.

6. The absorbent product of claim 5, wherein said release strip comprises kraft paper or calendered paper which is silicone treated on both sides.

7. An absorbent product having oppositely disposed ends and longitudinal edges comprising:
    an absorbent element having a body facing side and a garment facing side;
    a sheet of fluid impervious barrier material disposed on the garment facing side of said absorbent element and having a garment facing surface, said sheet having flaps extending from the longitudinal edges of said absorbent product:
    a fluid pervious cover disposed on the body facing side of said absorbent element, said cover having flaps extending from the longitudinal edges of said absorbent product which are generally co-extensive with the flaps of said sheet;
    adhesive means disposed on the garment facing surface of said sheet opposite said absorbent element and on the garment facing surface of said flaps of said sheet: and
    a release strip located on the garment facing surface of said sheet and having a first side covering said adhesive means which is opposite said absorbent element, said flaps being folded over said release strip with said adhesive means on said flaps opposing a second side of said release strip.

8. The absorbent product of claim 7, wherein said barrier material sheet and said cover comprise thermoplastic materials, said sheet and cover being thermally sealed to each other about their peripheries.

9. The absorbent product of claim 8, further comprising a layer of absorbent material disposed on the absorbent element facing side of said sheet of barrier material and being generally coextensive with said barrier material including said barrier material flaps.

10. A panty protector comprising a longitudinal body of fluid impervious material having flaps extending from opposite sides thereof, adhesive means centrally disposed on said longitudinal body and on the distal ends of said flaps, and a relese strip with a first side overlying said centrally disposed adhesive means, said flaps being folded over said release strip with the adhesive means of said flaps contacting a second side of said release strip.

11. An absorbent product having opposite ends and longitudinal edges comprising:
    an absorbent element having oppositely disposed longitudinal edges, a body facing side and a garment facing side:
    a fluid pervious cover overlying the body facing side and longitudinal edges of said absorbent element and having longitudinal edges;
    a fluid impervious barrier overlying the garment facing side of said absorbent element and bonded to said cover in the proximity of said longitudinal edges of said cover;

a sheet of fluid impervious material disposed between said barrier and said absorbent element and forming flaps extending outward from beneath opposite sides of said barrier, said sheet having a first side bonded to said barrier and a second side bonded to said cover.

12. The absorbent product of claim 11, further comprising a layer of absorbent material disposed on the side of said sheet which opposes said absorbent element.

13. The absorbent product of claim 12, further comprising adhesive means disposed on the side of said barrier facing away from said absorbent element, and on each of said flaps; and a release strip having a first side overlying said adhesive means on said barrier, wherein said flaps are folded over said release strip with the adhesive means disposed on said flaps contacting a second side of said release strip.

14. The absorbent product of claim 13, wherein said release strip is silicone treated on both sides.

15. An absorbent product comprising:
   an absorbent element having oppositely disposed longitudinal edges, a body facing side and a garment facing side;
   a fluid pervious cover overlying the body facing side of said absorbent element:
   a fluid impervious barrier overlying the garment facing side of said absorbent element, and cooperating with said cover to contain said absorbent element in a central area of said product; and
   first and second flaps extending respectively from respective longitudinal edges of said contained absorbent element area of said product and being of substantially unequal length such that said first flap extends a greater distance from its respective longitudinal edge than the extension of said second flap from its respective longitudinal edge.

16. The absorbent product of claim 15, further comprising adhesive means located over said barrier opposite said absorbent element and on said first flap proximate the extended end thereof.

17. The absorbent product of claim 16, further comprising a release strip having a first side covering said adhesive means located over said barrier.
   wherein said first flap is folded over said release strip with the adhesive means located on said first flap contacting a second side of said release strip.

18. The absorbent product of claim 17, wherein the combined lengths of said first and second flaps exceed the distance between said oppositely disposed edges of said absorbent element.

* * * * *